United States Patent [19]

Callahan et al.

[11] Patent Number: 4,468,385

[45] Date of Patent: Aug. 28, 1984

[54] POLY-CATION SALTS OF 4-O-POLY-HEXAOSE-THIO-ALKYLENE SULFATE DERIVATIVES AND METHOD OF USE

[75] Inventors: Francis M. Callahan, Stony Point; Thomas G. Miner, Sugarloaf; Seymour Bernstein, New City, all of N.Y.

[73] Assignee: American Cyanamid Company, Stamford, Conn.

[21] Appl. No.: 527,582

[22] Filed: Aug. 29, 1983

[51] Int. Cl.$^3$ ................ C07H 15/02; A61K 31/70
[52] U.S. Cl. ................................... 424/180; 536/4.1; 536/17.9; 536/18.2; 536/118; 536/122

[58] Field of Search .............. 536/4.1, 17.9, 18.6; 424/180

[56] References Cited

U.S. PATENT DOCUMENTS 4,399,126  8/1983  Schaub et al. ............... 536/4.1
4,404,365  9/1983  Miner et al. ................. 536/4.1

*Primary Examiner*—Johnnie R. Brown
*Attorney, Agent, or Firm*—A. M. Rosenblum

[57] ABSTRACT

Poly-cation salts of 4-O-polyhexaose-thio-alkylene sulfate derivatives, useful as modulators of the complement system, the intermediates thereof and the process of making such intermediates and products.

19 Claims, No Drawings

POLY-CATION SALTS OF 4-O-POLY-HEXAOSE-THIO-ALKYLENE SULFATE DERIVATIVES AND METHOD OF USE

BACKGROUND OF THE INVENTION

1. Field of the Invention

The present invention relates to novel cation salts of 4-O-polyhexaose-thio-alkylene sulfate derivatives, to their use as modulators of the complement system of warm-blooded animals, to the intermediates thereof and to the process for the preparation of such intermediates and products.

2. Description of the Prior Art

The term "complement" refers to a complex group of proteins in body fluids that, working together with antibodies or other factors, play an important role as mediators of immune, allergic, immunochemical and/or immunopathological reactions. The reactions in which complement participates take place in blood serum or in other body fluids, and hence are considered to be humoral reactions.

With regard to human blood, there are at present more than 20 proteins in the complement system consisting of the so-called classical and alternative pathways. These complement proteins are generally designated by the letter C and by number: C1, C2, C3 and so on up to C9. The complement protein C1 is actually an assembly of subunits designated C1q, C1r and C1s. The numbers assigned to the complement proteins reflect the sequence in which they become active, with the exception of complement protein C4, which reacts after C1 and before C2. The numerical assignments for the proteins in the complement system were made before the reaction sequence was fully understood. A more detailed discussion of the complement system and its biochemical, biological and pathological role in the body processes can be found in, for example, Bull. W. H. O. 39: 935 (1968); Annu. Rev. Med. 19: 1 (1968); Johns Hopkins Med. J. 128: 57 (1971); Harvey Lect. 66: 75 (1972); N. Engl. J. Med. 287; 452, 489, 545, 592, 642 (1972); Sci. Am. 229 (5): 54 (1973); Fed. Pro. 32: 134 (1973); Med. World, Oct. 11, 1974, p. 53; J. Allergy Clin. Immunol. 53: 298 (1974); Cold Spring Harbor Conf. Cell Proliferation 2/Proteases Biol. Control: 229 (1975); Annu. Rev. Biochem. 44: 697 (1975); Complement in Clinical Medicine, Dis. Mon. (1975); Complement, Scope, December 1975; Ann. Intern. Med. 84: 580 (1976); Transplant Rev.: 32 (1976); "Complement: Mechanisms and Functions," Prentice-Hall, Englewood Cliffs, N.J. (1976); Essays Med. Biochem. 2: 1 (1976); Hosp. Pract. 12: 33 (1977); Perturbation of Complement in Disease, Chap. 15 in Biol. Amplification Systems in Immunol. (Ed. Day and Good), Plenum, New York and London (1977); Am. J. Clin. Pathol. 68: 647 (1977); Biochem. Soc. Trans. 5: 1959 (1977); Harvey Lect. 72: 139 (1976–1977); J. Periodontol. 48: 505 (1977); Biochem. Soc. Trans. 6: 798 (1978); Clin. and Exp. Dermatol. 4: 271 (1979); Infect. Dis. Rev. 1: 483 (1979).

The complement system (e.g., classical pathway) can be considered to consist of three subsystems: (1) a recognition unit (C1q) which enables it to combine with antibody molecules that have detected a foreign invader; (2) an activation unit (C1r, C1s, C2, C4, C3) which prepares a site on the neighboring membrane; and (3) an attack unit (C5, C6, C7, C8 and C9) which creates a "hole" in the membrane. The membrane attack unit is nonspecific; it destroys invaders only because it is generated in their neighborhood. In order to minimize damage to the host's own cells, its activity must be limited in time. This limitation is accomplished partly by the spontaneous decay of activated complement and partly by interference by inhibitors and destructive enzymes. The control of complement, however, is not perfect, and there are times when damage is done to host's cells. Immunity is, therefore, a double-edged sword.

Activation of the complement system also accelerates blood clotting. This action comes about by way of the complement-mediated release of a clotting factor from platelets. The biologically active complement fragments and complexes can become involved in reactions that damage the host's cells. These pathogenic reactions can result in the development of immune-complex diseases. For example, in some forms of nephritis, complement damages the basal membrane of the kidney, resulting in the escape of protein from the blood into the urine. The disease disseminated lupus erythematosus belongs in this category; its symptoms include nephritis, visceral lesions and skin eruptions. The treatment of diphtheria or tetanus with the injection of large amounts of antitoxin sometimes results in serum sickness, an immune-complex disease. Rheumatoid arthritis also involves immune complexes. Like disseminated lupus erythematosus, it is an antoimmune disease in which the disease symptoms are caused by pathological effects of the immune system in the host's tissues. In summary, the complement system has been shown to be involved with inflammation, coagulation, fibrinolysis, antibody-antigen reactions and other metabolic processes.

In the presence of antibody-antigen complexes the complement proteins are involved in a series of reactions which may lead to irreversible membrane damage if they occur in the vicinity of biological membranes. Thus, while complement constitutes a part of the body's defense mechanism against infection it also results in inflammation and tissue damage in the immunopathological process. The nature of certain complement proteins, suggestions regarding the mode of complement binding to biological membranes and the manner in which complement effects membrane damage are discussed in Annu. Rev. Biochem. 38: 389 (1969); J. Exp. Med. 141: 724 (1975); J. Immunol. 116: 1431 (1976); 119: 1, 1195, 1358, 1482 (1977); 120: 1841 (1978); Immunochemistry 115: 813 (1978); J. Biol. Chem. 254: 9908 (1979).

A variety of substances have been disclosed as inhibiting the complement system, i.e., as complement inhibitors. For example, the compounds, 3,3'-ureylenebis[6-(2-amino-8-hydroxy-6-sulfo-1-naphthylazo)benzenesulfonic acid], tetrasodium salt (chlorazol fast pink), heparin and a sulphated dextran have been reported to have an anticomplementary effect, Br. J. Exp. Pathol. 33: 327 (1952). German Pat. No. 2,254,893 or South African Pat. No. 727,923 discloses certain 1-(diphenylmethyl)-4(3-phenylallyl)piperazines useful as complement inhibitors. Other chemical compounds having complement inhibiting activity are disclosed in, for example, J. Med. Chem. 12: 415, 902, 1049, 1053 (1969); Can. J. Biochem. 47: 547 (1969); J. Immunol. 104: 279 (1970); J. Immunol. 106: 241 (1971); J. Immunol. 111: 1061 (1973); Biochim. Biophys. Acta 317: 539 (1973); Life Sci. 13: 351 (1973); J. Immunol. 113: 584 (1974); Immunology 26: 819

(1974); J. Med. Chem. 17: 1160 (1974); Biochim. Biophys. Res. Comm. 67: 225 (1975); Ann. N.Y. Acad. Sci. 256: 441 (1975); J. Med. Chem. 19: 634, 1079 (1976); J. Immunol. 118: 466 (1977); Arch. Int. Pharmacodyn. 226: 281 (1977); Biochem. Pharmacol. 26: 325 (1977); J. Pharm. Sci. 66: 1367 (1977); Chem. Pharm. Bull. 25: 1202 (1977); Biochim. Biophys. Acta 484: 417 (1977); J. Clin. Microbiol. 5: 278 (1977); Immunochemistry 15: 231 (1978); Immunology 34: 509 (1978); J. Exp. Med. 147: 409 (1978); Thromb. Res. 14: 179 (1979); J. Immunol. 122: 2418 (1979); J. Chem. Soc. Chem. Comm. 726 (1979); Immunology 36: 131 (1979); Biochim. Biophys. Acta 611: 196 (1980); and J. Med. Chem. 23: 240 (1980).

It has been reported that the known complement inhibitors, epsilon-aminocaproic acid and tranexamic acid, have been used with success in the treatment of hereditary angioneurotic edema, a disease state resulting from an inherited deficiency or lack of function of the serum inhibitor of the activated first component of complement (C1 inhibitor), N. Engl. J. Med. 286: 808 (1972); 287: 452 (1972); Ann. Intern. Med. 84: 580 (1976); J. Allergy Clin. Immunol. 60: 38 (1977). Also androgenic steroids have been used successfully in the treatment of this physiological disorder; see Medicine 58: 321 (1979); Arthritis Rheum. 22: 1295 (1979); Am. J. Med. 66: 681 (1979); and J. Allergy Clin. Immunol. 65: 75 (1980).

It has also been reported that the drug pentosan-polysulfoester has an anticomplementary activity on human serum, both in vitro and in vivo, as judged by the reduction in total hemolytic complement activity, Pathol. Biol. 25: 33; 25 (2): 105; 25 (3): 179 (1977).

SUMMARY OF THE INVENTION

This invention relates to new compounds which are 4-O-polyhexaose-thio-alkylene sulfate derivatives and the cation salts thereof, that modulate the complement system, thereby modulating complement activity in body fluids. Moreover this invention involves a method of modulating the complement system in a body fluid which comprises subjecting body fluid complement to the action of an effective complement modulating amount of the above-identified compounds. This invention further concerns a method of modulating the complement system in a warm-blooded animal which comprises administering to said animal an effective complement modulating amount of the above-identified compounds.

This invention also deals with the novel precursors that act as intermediates in preparing the above-described complement modulating compounds.

DETAILED DESCRIPTION OF THE INVENTION

In accordance with the present invention there are provided novel compounds represented by the following generic formula I:

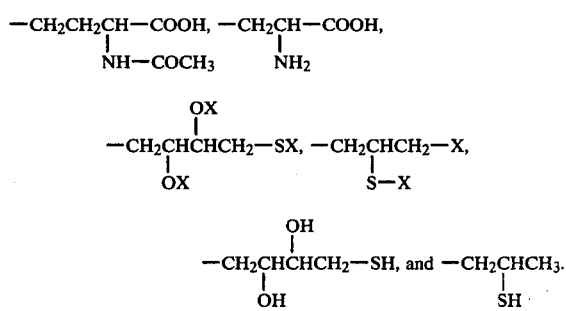

Formula I

-continued ($\sim$ = α or β)

wherein X is —SO$_3$M and M is a nontoxic pharmaceutically acceptable cation salt, wherein the salt forming moiety is selected from the group consisting of alkali metal, alkaline earth metal, aluminum, ammonia, zinc and substituted ammonia selected from the group consisting of trialkylamine (C$_1$–C$_6$), piperidine, pyrazine, alkanolamine (C$_2$–C$_6$) and cycloalkylamine (C$_3$–C$_6$); and R$_1$ is selected from the group consisting of

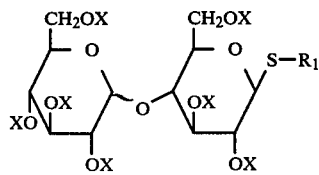

Particularly preferred compounds of formula I which are of major interest as modulators of the complement system include the following:

2,3-dihydroxy-4-mercaptobutyl-2,3,6-tri-O-sulfo-4-O-(2,3,4,6-tetra-O-sulfo-α-D-glucopyranosyl)-1-thio-β-D-glucopyranoside heptasodium salt 2,3-dihydroxy-4-mercaptobutyl-2,3,6-tri-O-sulfo-4-O-(2,3,4,6-tetra-O-sulfo-α-D-glucopyranosyl)-1-thio-β-D-glucopyranoside hexatriethylammonium salt 3-hydroxy-2-mercaptopropyl-2,3,6-tri-O-sulfo-4-O-(2,3,4,6-tetra-O-sulfo-α-D-glucopyranosyl)-1-thio-β-D-glucopyranoside nonasodium salt 3-hydroxy-2-mercaptopropyl 2,3,6-tri-O-sulfo-4-O-(2,3,4,6-tetra-O-sulfo-α-D-glucopyranosyl)-1-thio-β-D-glucopyranoside nonatriethylammonium salt S-[2,3,6-tri-O-sulfo-4-O-(2,3,4,6-tetra-O-sulfo-α-D-glucopyranosyl)-β-D-glucopyranosyl]-L-cysteine heptasodium salt S-[2,3,6-tri-O-sulfo-4-O-(2,3,4,6-tetra-O-sulfo-α-D-glucopyranosyl)-β-D-glucopyranosyl]-L-cysteine heptatriethylammonium salt S-[2,3,6-tri-O-sulfo-4-O-(2,3,4,6-tetra-O-sulfo-α-D-glucopyranosyl)-β-D-glucopyranosyl]-2-acetamido-4-mercaptobutyric acid heptasodium salt S-[2,3,6-tri-O-sulfo-4-O-(2,3,4,6-tetra-O-sulfo-α-D-glucopyranosyl)-β-D-glucopyranosyl]-2-acetamido-4-mercaptobutyric acid heptatriethylammonium salt Although the compounds of formula I are shown as being fully sulfated, this invention is not restricted to such and partially sulfated compounds are contemplated herein.

This invention further deals with a method of modulating the complement system in a body fluid, such as blood serum, which comprises subjecting body fluid complement to the action of an effective complement modulating amount of a compound of the above formula I. Body fluids can include blood, plasma, serum, synovial fluid, cerebrospinal fluid, or pathological accumulations of fluid such as pleural effusion, etc. This invention also concerns a method of modulating the complement system in a warm-blooded animal which comprises administering to said animal an effective complement modulating amount of a compound of the above formula I.

In addition this invention is concerned with the precursors in the preparation of the complement modulating compounds of formula I, shown by the following formula II:

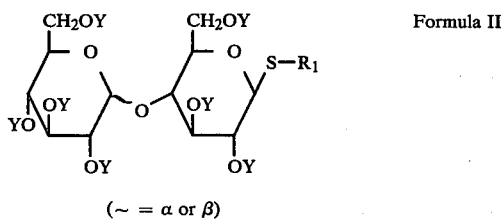

(∼ = α or β)

wherein Y is selected from the group consisting of H and COCH₃ and R₁ is selected from the group consisting of

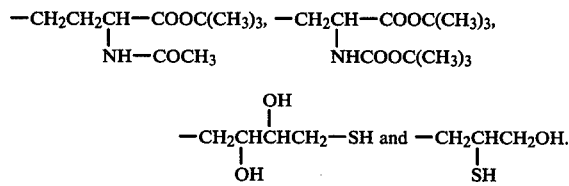

Specific compounds of formula II which are of particular interest as intermediates for the production of the compounds of formula I include the following:

2,3-dihydroxy-4-mercaptobutyl-2,3,6-tri-O-acetyl-4-O-(2,3,4,6-tetra-O-acetyl-α-D-glucopyranosyl)-1-thio-β-D-glucopyranoside 2,3-dihydroxy-4-mercaptobutyl-4-O-(α-D-glucopyranosyl)-1-thio-β-D-glucopyranoside 3-hydroxy-2-mercaptopropyl-2,3,6-tri-O-acetyl-4-O-(2,3,4,6-tetra-O-acetyl-α-D-glucopyranosyl)-1-thio-β-D-glucopyranoside 3-hydroxy-2-mercaptopropyl-4-O-(α-D-glucopyranosyl)-1-thio-β-D-glucopyranside S-[2,3,6-tri-O-acetyl-4-O-(2,3,4,6-tetra-O-acetyl-α-D-glucopyranosyl)-β-D-glucopyranosyl]-L-cysteine, N-carboxy di tert. butyl ester 4-O-(α-D-glucopyranosyl)-β-D-glucopyranosyl-L-N-tertiary-butyloxycarbonylcysteine, tertiary-butyl ester S-[2,3,6-tri-O-acetyl-4-O-(2,3,4,6-tetra-O-acetyl-α-D-glucopyranosyl)-β-D-glucopyranosyl]-2-acetamido-4-mercaptobutyric acid, tertiary-butyl ester S-[4-O-(α-D-glucopyranosyl)-β-D-glucopyranosyl]-2-acetamido-4-mercaptobutyric acid, tertiary-butyl ester In the above formulas I and II the sugar molecule is drawn to represent either maltose or cellobiose. This invention is not restricted to these two disaccharides, but instead is intended to include disaccharides consisting of aldohexoses, ketohexoses, aldopentoses and the like as well as other polysaccharides such as maltotrioses, pentoses or uronic acids.

The compounds of Formula I find utility as complement modulators in body fluids and as such may be used to ameliorate or prevent those pathological reactions requiring the function of complement and in the therapeutic treatment of warm-blooded animals having immunologic diseases such as rheumatoid arthritis, systemic lupus erythematosus, certain kinds of glomerulonephritis, certain kinds of autoallergic hemolytic anemia, certain kinds of platelet disorders and certain kinds of vasculitis. These compounds may also be used in the therapeutic treatment of warm-blooded animals having nonimmunologic diseases such as paroxysmal nocturnal hemoglobinurea, hereditary angioneurotic edema and inflammatory states induced by the action of bacterial or lysosomal enzymes on the appropriate complement components as, for example inflammation following coronary occlusion. They also may be useful in the treatment of transplant rejection and ulcers and as blood culture and transport mediums. The sulfated compounds of this invention such as the sodium and aluminum salts, may be particularly useful in the treatment of ulcers and the like on oral therapy. Also, the non-sulfated intermediate compounds of Formula II may be useful as immuno-enhancing agents or potentiators.

The compounds of this invention may be prepared according to the following flowchart.

FLOWCHART

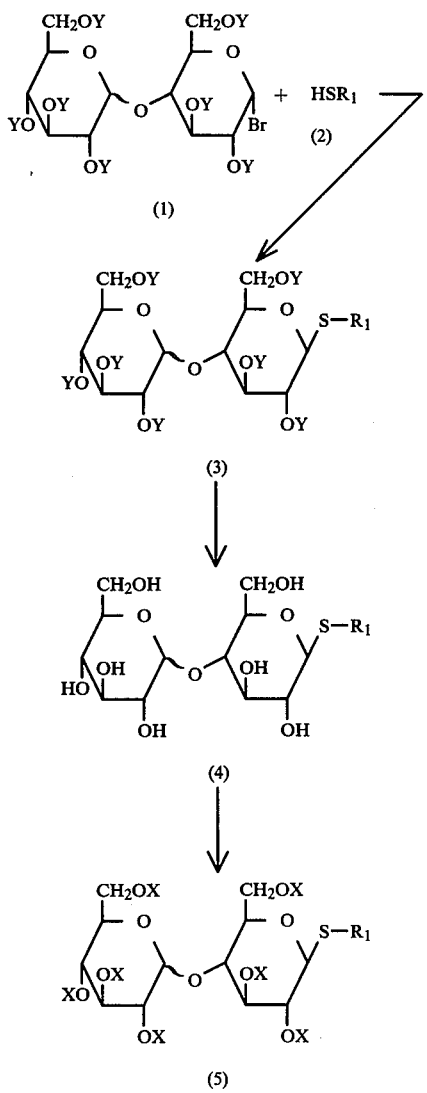

In accordance with the above flowchart, an α-bromo polyacetyl disaccharide where Y is —COCH₃ (1) (here represented by α-acetobromomaltose) is reacted with a solution of a mercapto derivative (2), where $R_1$ is as hereinabove described and tetrabutylphosphonium bromide at $-5°$ to $+5°$ C. for an hour, then at room temperature for 18-36 hours, extracted with ethyl acetate and purified by chromatography giving a substituted 4-[2,3,6-tri-O-acetyl-4-O-(2,3,4,6-tetra-O-acetyl-α(or β)-D-glucopyranosyl)-1-thio-β-D-glucopyranoside, where Y is $COCH_3$ which is then reacted with sodium in anhydrous methanol for several hours giving a substituted 4-O-[α(or β)-D-glucopyranosyl]-1-thio-β-D-glucopyranoside (4) which is then reacted with trialkylamine ($C_1$-$C_6$) sulfur trioxide complex in N,N-dimethylacetamide at 60°-70° C. for several hours, giving the polytrialkylamine salt of a substituted 4-[2,3,6-tri-O-sulfo-4-O-(2,3,4,6-tetra-O-sulfo-α(or β)-D-glucopyranosyl)-1-thio-β-D-glucopyranoside (5), where X is $-SO_3M$ and M is $NH^+$ [alkyl ($C_1$-$C_6$)]$_3$, which is then reacted with a cation-containing compound wherein the salt forming moiety is selected from the group consisting of alkali metal, alkaline earth metal, aluminum, zinc, ammonia and substituted ammonia selected from the group consisting of piperidine, pyrazine, alkanolamine ($C_2$-$C_6$) cycloalkylamine ($C_3$-$C_6$), and then precipitated in ethanol, giving (5) as the end product, where X and $R_1$ are as described above in formula I.

It is generally preferred that the respective product of each process step, described hereinabove, is separated and/or isolated prior to its use as starting material for subsequent steps. Separation and isolation can be effected by any suitable purification procedure such as, for example, evaporation, crystallization, column chromatography, thin-layer chromatography, etc. Also it should be appreciated that when typical reaction conditions (e.g., temperatures, mole ratios, reaction times) have been given, the conditions which are both above and below these specified ranges can also be used, though generally less conveniently.

The term "pharmaceutically acceptable salt" refers to those salts of the parent compound which do not significantly or adversely affect the pharmaceutical properties (e.g., toxicity, effectiveness, etc.) of the parent compound. The salt forming moieties of the present invention which are pharmaceutically acceptable include the alkali metals (e.g., sodium, potassium, etc.); alkaline earth metals (e.g., calcium, etc.); aluminum; zinc; ammonia; and substituted ammonia selected from the group consisting of trialkylamine ($C_1$-$C_6$), piperidine, pyrazine, alkanolamine ($C_2$-$C_6$) and cycloalkylamine ($C_3$-$C_6$).

The term "trialkylamine ($C_1$-$C_6$)" defines those amines having three aliphatic fully saturated hydrocarbon substituents containing 1 to 6 carbon atoms either linearly or branched. Typically, these amines are trimethylamine, triethylamine, tripropylamine, dimethylethylamine, dimethyl-1-propylamine, etc. The term "alkanolamine ($C_2$-$C_6$)" refers to the above-defined trialkylamines additionally substituted with at least one and not more than three hydroxy groups on at least two of the alkyl hydrocarbon chains. Such amines are, for example, triethanolamine, tripropanolamine, etc. The term "cycloalkylamine ($C_3$-$C_6$)" is defined as the 3 to 6 fully saturated carbocyclic moieties such as cyclopropyl, methylcyclobutyl, cyclopentyl, cyclohexyl, etc.

As used hereinabove and below unless expressly stated to the contrary, all temperatures and temperature ranges refer to the centrigrade system and the terms "ambient" or "room temperature" refer to about 25° C. The term "percent" or "(%)" refers to weight percent and the terms "mole" and "moles" refer to gram moles. The term "equivalent" refers to a quantity of reagent equal in moles to the moles of the preceding or succeeding reactant recited in the Preparation or Example in the term of moles of finite weight or volume.

Whereas the exact scope of the instant invention is set forth in the appended claims, the following specific examples illustrate certain aspects of the present invention. However, the examples are set forth for illustration only and are not to be construed as limitations on the present invention except as set forth in the appended claims.

A further understanding of the invention can be obtained from the following non-limiting Preparations and Examples.

EXAMPLE 1

2,3,-Dihydroxy-4-mercaptobutyl 2,3,6-tri-O-acetyl-4-O-(2,3,4,6-tetra-O-acetyl-α-D-glucopyranosyl]-1-thio-β-D-glucopyranoside To a solution of 2.3 g of sodium hydroxide in 3 of water at 0° C. was added in sequence 4.4 g of dithioerythritol, 50 ml of toluene, 10.0 g of α-acetobromomaltose and 0.25 g of tetrabutylphosphonium bromide. The reaction was stirred at $-5°$ C. for one hour, then allowed to warm to room temperature. After standing 24 hours the reaction was diluted with 50 ml of ethyl acetate and 50 ml of water. The two phase solution was filtered. The phases were separated and the organic layer was extracted with 25 ml of water. The organic layer was dried, and concentrated in vacuo giving an oil. This oil was chromatographed [chloroform:ethyl acetate:ethanol (90:10:2)] giving 2.1 g of liquid which was rechromatographed [methylene chloride:ethanol (97:13)], giving 1.42 g of the desired intermediate as a glass, $[\alpha]_D^{26°} = +46°$.

EXAMPLE 2

2,3-Dihydroxy-4-mercaptobutyl 4-O-(α-D-glucopyranosyl)-1-thio-β-D-glucopyranoside A 50 mg portion of hexane washed sodium spheres was added to a solution of 1.3 g of 2,3-dihydroxy-4-mercaptobutyl-4-[2,3,6-tri-O-acetyl-4-O-(2,3,4,6-tetra-O-acetyl-α-D-glucopyranosyl)-1-thio-β-D-glucopyranoside] in 15 ml of anhydrous methanol. After 3 hours the reaction was diluted with an equal volume of ether. The solid was collected, washed with ether and dried in vacuo, giving 0.6 g of the desired intermediate as a white solid, $[\alpha]_D^{26°} = +50°$ ($CH_3OH$).

EXAMPLE 3

2,3-Dihydroxy-4-mercaptobutyl 2,3,6-tri-O-sulfo-4-O-(2,3,4,6-tetra-O-sulfo-α-D-glucopyranosyl)-1-thio-β-D-glucopyranoside heptasodium salt A solution of 0.5 g of 2,3-dihydroxy-4-mercaptobutyl-4-O-(α-D-glucopyranosyl)-1-thio-β-D-glucopyranoside, 1.0 g of 4 Å molecular sieves and 3.76 g of triethylamine sulfur trioxide complex in 4 ml of N,N-dimethylacetamide was stirred at 65° C. overnight. The reaction was filtered while warm into 200 ml of acetone. (This solution contained the heptatriethylammonium derivative). The acetone solution was decanted and the semi-solid residue dissolved in 10 ml of water containing 1.1 g of sodium acetate. This mixture was filtered into 450 ml of ethanol, then chilled and the resulting solid collected, giving 1.37 g of the desired product as a white solid, $[\alpha]_D^{26°} = +25°$ (water).

EXAMPLE 4

3-Hydroxy-2-mercaptopropyl 2,3,6-tri-O-acetyl-4-O-(2,3,4,6-tetra-O-acetyl-α-D-glucopyranosyl)-1-thio-β-D-glucopyranoside A reaction mixture comprising 7.0 g of α-acetobromomaltose, 6.0 g of 2,3-dimercaptopropanol, 5.0 ml of 10 N sodium hydroxide, 200 mg of benzyltriethylammonium chloride and 100 ml of toluene was stirred at room temperature under argon for 76 hours. The organic layer was separated, dried and concentrated in vacuo to an oil. This oil was chromatographed [ethyl acetate:hexane (1:1)] giving 1.2 g of the desired intermediate as a solid, $[\alpha]_D^{26°} = +51°$ (CH$_3$OH).

EXAMPLE 5

3-Hydroxy-2-mercaptopropyl 4-O-(α-D-glucopyranosyl)-1-thio-β-D-glucopyranoside

A solution of 4.1 g of 3-hydroxy-2-mercaptopropyl-4-[2,3,6-tri-O-acetyl-4-O-(2,3,4,6-tetra-O-acetyl-α-D-glucopyranosyl)]-1-thio-β-D-glucopyranoside] in 51 ml of 2 N methanolic triethylamine [triethylamine:methanol:water (3:6:2)] was stirred for 16 hours then concentrated to a solid. This solid was refluxed with 50 ml of methylene chloride then decanted, giving 2.8 g of the desired intermediate, $[\alpha]_D^{26°} = +50°$.

EXAMPLE 6

3-Hydroxy-2-mercaptopropyl 4-[2,3,4,6-tetra-O-sulfo-α-D-glucopyranosyl]-1-thio-2,3,6-tri-O-sulfo-β-D-glucopyranoside nonasodium salt A solution of 3.9 g of 1-(3-hydroxy-2-mercaptopropyl) 4-O (α-D-glucopyranosyl)-1-thio-β-D-glucopyranoside and 13.5 g of triethylamine-sulfur trioxide complex in 15 ml of dry dimethylacetamide was heated at 65° C. for 16 hours under argon. The solution was poured into acetone and the solvent decanted. The semi solid was dissolved in water containing sodium acetate (1.3 g) and after 1½ hours this solution was poured into 200 ml of ethanol. The solid was collected giving 6.0 g, $[\alpha]_D^{26°} = +12°$.

EXAMPLE 7

3-Hydroxy-2-mercaptopropyl 4-O-α-D-glucopyranosyl-1-thio-β-D-glucopyranoside-tetrakis-(H-sulfate) tetrasodium salt A solution of 2.3 g of (3-hydroxy-2-mercaptopropyl 4-O-(α-D-glucopyranosyl)-1-thio-β-D-glucopyranoside and 12.5 g of triethylamine-sulfur trioxide complex in 15 ml of dry dimethylacetamide was stirred under argon overnight at room temperature. The reaction was poured into 300 ml of dry acetone and the solution decanted from the residue. The residue was dissolved in 15 ml of water containing 4.1 g of sodium acetate and 1 g of Bio Rad ®70 Na+) (polycarboxylic acid) resin. This slurry was filtered into 300 ml of absolute ethanol and the solid collected giving 3.9 g $[\alpha]_D^{26°}$ C. = +5°.

EXAMPLE 8

4-[2,3,6-Tri-O-acetyl-4-O-(2,3,4,6-tetra-O-acetyl-α-D-glucopyranosyl)-β-D-glucopyranosyl]-L-N-tertiary-butyloxycarbonyl tert. butyl ester L-S-benzylcysteine tert. butyl ester was (prepared by the method of R. W. Roeske, Chem. and Ind., 1121, Sept. 5, 1959), was converted to L-N-tertiary-butyloxycarbonyl-S-benzyl cysteine tert. butyl ester using di-tertiarybutyl dicarbonate, as discribed by L. Morodes, et al. Hoppe Seyler's Z. Physiol. Chem., 357, 1651 (1976).

Removal of the benzyl group was accomplished by adding L-N-tertiarybutyloxycarbonyl-S-benzylcysteine to liquid ammonia and then adding sodium until a blue color persisted giving L-N-tertiarybutyloxycarbonylcysteine tert. butyl ester.

A portion of this ester was converted to the sodium derivative by treatment with an equivalent of soduim hydride in anhydrous tetrahydrofuran.

To a stirred mixture of 3.05 g of the sodium thioalcoholate derivative of L-N-tertiary-butyloxycarbonylcysteine tert. butyl ester in 50 ml of tetrahydrofuran was added 7.0 g of heptaacetyl-α-bromomaltose. After stirring for 3 days the mixture was filtered and the product recovered from the filtrate. This crude product was purified by column chromatography on silica gel, giving 1.58 g of the desired intermediate as a light yellow amorphous powder.

NMR analysis confirmed the structure: 1.9–2.1(21-CH$_3$-CO) and 1.42(18H,t.Bu).

EXAMPLE 9

4-O-(α-D-Glucopyranosyl)-β-D-glucopyranosyl-L-N-tertiarybutyloxycarbonylcysteine tertiarybutyl ester To 500 mg of 4-[2,3,6-tri-O-acetyl-4-O-(2,3,4,6-tetra-O-acetyl-α-D-glucopyranosyl)-β-D-glucopyranosyl]-L-N-tertiarybutyloxycarbonylcysteine tertiarybutyl ester in 5 ml of methanol was added 10 mg of sodium metal. After 30 minutes a portion of acetic acid was added and the mixture was concentrated in vacuo to a residue, giving 400 mg of the desired intermediate. The absence of acetyl groups and the presence of tert. butyl groups were confirmed by NMR data.

EXAMPLE 10

4-[2,3,6-Tri-O-sulfo-4-O-(2,3,4,6-tetra-O-sulfo-α-D-glucopyranosyl)-β-D-glucopyranosyl]-L-cysteine heptasodium salt A 240 mg portion of 4-O-(α-D-glucopyranosyl)-β-D-glucopyranosyl-L-N-tertiary-butyloxycarbonylcysteine tertiary-butyl ester and 1.45 g of triethylamine-sulfur trioxide complex were dissolved in 25 ml of N,N-dimethylacetamide under nitrogen and held at 65° C. for 20 hours. The mixture was added to 125 ml of methyl isobutyl ketone and then filtered through a pad of diatomaceous earth. The pad was washed with water and this aqueous filtrate was treated with an ion exchange resin (Na+ form) and then freeze dried giving 186 mg of the desired product as a powder, $[\alpha]_D^{26°} = +13 \pm 3°$ (0.335%, water). The N-tertiarybutyloxycarbonyl and tert. butyl ester groups are removed during the persulfation procedure.

EXAMPLE 11

4-[2,3,6-Tri-O-acetyl-4-O-(2,3,4,6-tetra-O-acetyl-α-D-glucopyranosyl]-2-acetamido-4-mercaptobutyric acid tert.-butyl ester D-N-acetyl-S-benzylhomocysteine was converted to the corresponding D-N-acetyl-S-benzylhomocysteine tert. butyl ester by the procedure of R. W. Roeske, Chem. and Ind; 1121, Sept. 5, 1959. The product was isolated as a colorless oil.

Treatment of this oil in liquid ammonia with metallic sodium until a deep blue color persisted removed the S-benzyl protecting group giving D-N-acetylhomocysteine tert. butyl ester as a crystalline solid.

A 1.025 g portion of this solid, 2.94 g of heptacetylbromomaltose, 0.55 g of potassium carbonate, 5 ml of water and 10 ml of acetone were reacted for 14 days and then purified by column chromatography on silica gel, giving 707 mg of the desired product as a colorless powder. The structure was confirmed by chemical analysis and NMR 1.42 (9H,t,Bu).

EXAMPLE 12

4-O-(α-D-Glucopyranosyl)-β-D-glucopyranosyl-2-acetamido-4-mercaptobutyric acid tertiary-butyl ester A 650 mg portion of 4-[2,3,6-tri-O-acetyl-4-O-(2,3,4,6-tetra-O-acetyl-α-D-glucopyranosyl)-β-D-glucopyranosyl]-2-acetamido-4-mercaptobutyric acid tertiary butyl ester in 25 ml of absolute methanol was treated with a catalytic amount of sodium. After 10 minutes the solution was washed with ethyl acetate:hexane (1:1), the methanol was then removed in vacuo and the residue treated with 25 ml of water and filtered through diatomaceous earth. This filtrate was freeze-dried, giving 445 mg of the desired intermediate.

The product gave a single spot on TLC, Rf 0.30, using the solvent system $CH_2Cl_2-CH_3OH=5:1$ on silica.

EXAMPLE 13

4-[2,3,6-Tri-O-sulfo-4-O-(2,3,4,6-tetra-O-sulfo-α-D-glucopyranosyl)-β-D-glucopyranosyl]-2-acetamido-4-mercaptobutyric acid heptasodium salt A 334 mg portion of 4-O-(α-D-glucopyranosyl)-β-D-glucopyranosyl-2-acetamido-4-mercaptobutyric acid tertiary-butyl ester and 2.172 g of triethylamine-sulfur trioxide complex in 25 ml of N,N-dimethylacetamide over molecular sieves was reacted as described in Example 10 giving 590 mg of the desired product as a white powder. The tert. butyl ester was removed during the persulfation procedure.

EXAMPLE 14

Preparation of Compressed Tablet

| Ingredient | mg./Tablet |
| --- | --- |
| Active Compound | 0.5–500 |
| Dibasic Calcium Phosphate N.F. | qs |
| Starch USP | 40 |
| Modified Starch | 10 |
| Magnesium Stearate USP | 1–5 |

EXAMPLE 15

Preparation of Compressed Tablet—Sustained Action

| Ingredient | mg./Tablet |
| --- | --- |
| Active Compound as Aluminum Lake*, Micronized | 0.5–500 (as acid equivalent) |
| Dibasic Calcium Phosphate N.F. | qs |
| Alginic Acid | 20 |
| Starch USP | 35 |
| Magnesium Stearate USP | 1–10 |

*Complement modulator plus aluminum sulfate yields aluminum complement modulator. Complement modulator content in aluminum lake ranges from 5–30%.

EXAMPLE 16

Preparation of Hard Shell Capsule

| Ingredient | mg./Capsule |
| --- | --- |
| Active Compound | 0.5–500 |
| Lactose, Spray Dried | qs |
| Magnesium Stearate | 1–10 |

EXAMPLE 17

Preparation of Oral Liquid (Syrup)

| Ingredient | % W/V |
| --- | --- |
| Active Compound | 0.05–5 |
| Liquid Sugar | 75.0 |
| Methyl Paraben USP | 0.18 |
| Propyl Paraben USP | 0.02 |
| Flavoring Agent | qs |
| Purified Water qs ad | 100.0 |

EXAMPLE 18

Preparation of Oral Liquid (Elixir)

| Ingredient | % W/V |
| --- | --- |
| Active Compound | 0.05–5 |
| Alcohol USP | 12.5 |
| Glycerin USP | 45.0 |
| Syrup USP | 20.0 |
| Flavoring Agent | qs |
| Purified Water qs ad | 100.0 |

EXAMPLE 19

Preparation of Oral Suspension (Syrup)

| Ingredient | % W/V |
| --- | --- |
| Active Compound as Aluminum Lake, Micronized | 0.05–5 (acid equivalent) |
| Polysorbate 80 USP | 0.1 |
| Magnesium Aluminum Silicate, Colloidal | 0.3 |
| Flavoring Agent | qs |
| Methyl Paraben USP | 0.18 |
| Propyl Paraben USP | 0.02 |
| Liquid Sugar | 75.0 |
| Purified Water qs ad | 100.0 |

EXAMPLE 20

Preparation of Injectable Solution

| Ingredient | % W/V |
|---|---|
| Active Compound | 0.05–5 |
| Benzyl Alcohol N.F. | 0.9 |
| Water for Injection | 100.0 |

EXAMPLE 21

Preparation of Injectable Oil

| Ingredient | % W/V |
|---|---|
| Active Compound | 0.05–5 |
| Benzyl Alcohol | 1.5 |
| Sesame Oil qs ad | 100.0 |

EXAMPLE 22

Preparation of Intra-Articular Product

| Ingredient | Amount |
|---|---|
| Active Compound | 2–20 mg. |
| NaCl (physiological saline) | 0.9% |
| Benzyl Alcohol | 0.9% |
| Sodium Carboxymethylcellulose | 1–5% |
| pH adjusted to 5.0–7.5 | |
| Water for Injection qs ad | 100% |

EXAMPLE 23

Preparation of Injectable Depo Suspension

| Ingredient | % W/V |
|---|---|
| Active Compound | 0.05–5 (acid equivalent) |
| Polysorbate 80 USP | 0.2 |
| Polyethylene Glycol 4000 USP | 3.0 |
| Sodium Chloride USP | 0.8 |
| Benzyl Alcohol N.F. | 0.9 |
| HCl to pH 6–8 | qs |
| Water for Injection qs ad | 100.0 |

EXAMPLE 24

Preparation of Dental Paste

| Ingredient | % W/V |
|---|---|
| Active Compound | 0.05–5 |
| Zinc Oxide | 15 |
| Polyethylene Glycol 4000 USP | 50 |
| Distilled Water qs | 100 |

EXAMPLE 25

Preparation of Dental Ointment

| Ingredient | % W/W |
|---|---|
| Active Compound | 0.05–5 |
| Petrolatum, White USP qs | 100 |

EXAMPLE 26

Preparation of Dental Cream

| Ingredient | % W/W |
|---|---|
| Active Compound | 0.05–5 |
| Mineral Oil | 50 |
| Beeswax | 15 |
| Sorbitan Monostearate | 2 |
| Polyoxyethylene 20 Sorbitan Monostearate | 3 |
| Methyl Paraben USP | 0.18 |
| Propyl Paraben USP | 0.02 |
| Distilled Water qs | 100 |

EXAMPLE 27

Preparation of Topical Cream

| Ingredient | % W/W |
|---|---|
| Active Compound | 0.05–5 |
| Sodium Lauryl Sulfate | 1 |
| Propylene Glycol | 12 |
| Stearyl Alcohol | 25 |
| Petrolatum, White USP | 25 |
| Methyl Paraben USP | 0.18 |
| Propyl Paraben USP | 0.02 |
| Purified Water qs | 100 |

EXAMPLE 28

Preparation of Topical Ointment

| Ingredient | % W/W |
|---|---|
| Active Compound | 0.05–5 |
| Cholesterol | 3 |
| Stearyl Alcohol | 3 |
| White Wax | 8 |
| Petrolatum, White USP qs | 100 |

EXAMPLE 29

Preparation of Spray Lotion (Non-aerosol)

| Ingredient | % W/W |
|---|---|
| Active Compound | 0.05–5 |
| Isopropyl Myristate | 20 |
| Alcohol (Denatured) qs | 100 |

EXAMPLE 30

Preparation of Buccal Tablet

| Ingredient | g./Tablet |
|---|---|
| Active Ingredient | 0.00325 |
| 6x Sugar | 0.29060 |
| Acacia | 0.01453 |
| Soluble Starch | 0.01453 |
| F. D. & C. Yellow No. 6 Dye | 0.00049 |
| Magnesium Stearate | 0.00160 |
| | 0.32500 |

The final tablet will weigh about 325 mg. and may be compressed into buccal tablets in flat faced or any other tooling shape convenient for buccal administration.

EXAMPLE 31

Preparation of Lozenge

| Ingredient | g./Lozenge |
| --- | --- |
| Active Ingredient | 0.0140 |
| Kompact ® Sugar (Sucrest Co.) | 0.7138 |
| 6x Sugar | 0.4802 |
| Sorbitol (USP Crystalline) | 0.1038 |
| Flavor | 0.0840 |
| Magnesium Stearate | 0.0021 |
| Dye | qs |
| Stearic Acid | 0.0021 |
| | 1.4000 |

The ingredients are compressed into ⅜" flat based lozenge tooling. Other shapes may also be utilized.

The compounds of the present invention may be administered internally, e.g., orally, intra-articularly or parenterally, to a warm-blooded animal to inhibit complement in the body fluid of the animal, such inhibition being useful in the amelioration or prevention of those reactions dependent upon the function of complement such as inflammatory process and cell membrane damage induced by antigen-antibody complexes. A range of doses may be employed depending on the mode of administration, the condition being treated and the particular compound being used. For example, for intravenous or subcutaneous use from about 5 to about 50 mg/kg/day, or every six hours for more rapidly excreted salts, may be used. For intra-articular use for large joints such as the knee, from about 2 to about 20 mg/joint/week may be used, with proportionally smaller doses for smaller joints. The dosage range is to be adjusted to provide optimum therapeutic response in the warm-blooded animal being treated. In general, the amount of compound administered can vary over a wide range to provide from about 5 mg/kg to about 100 mg/kg of body weight of animal per day. The usual daily dosage for a 70 kg subject may vary from about 350 mg to about 3.5 g. Unit doses of the acid or salt can contain from about 0.5 mg to about 500 mg.

The compounds of the present invention may also be administered topically in the form of ointments, creams, lotions and the like, suitable for the treatment of complement dependent dermatological disorders.

Moreover, the compounds of the present invention may be administered in the form of dental pastes, ointments, buccal tablets and other compositions suitable for application periodontally for the treatment of periodontitis and related diseases of the oral cavity.

In therapeutic use, the compounds of this invention may be administered in the form of conventional pharmaceutical compositions. Such compositions may be formulated so as to be suitable for oral or parenteral administration. The active ingredient may be combined in admixture with a pharmaceutically acceptable carrier, which carrier may take a wide variety of forms depending on the form of preparation desired for administration, i.e., oral or parenteral. The compounds can be used in compositions such as tablets. Here, the principal active ingredient is mixed with conventional tabletting ingredients such as corn starch, lactose, sucrose, sorbitol, talc, stearic acid, magnesium stearate, dicalcium phosphate, gums, or similar materials as non-toxic pharmaceutically acceptable diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly avantageous enteric coating comprises a styrene maleic acid copolymer together with known materials contributing to the enteric properties of the coating. The tablet or pill may be colored through the use of an appropriate nontoxic dye, so as to provide a pleasing appearance.

The liquid forms in which the novel compositions of the present invention may be incorporated for administration include suitable flavored emulsions with edible oils, such as, cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The term "dosage form", as described herein, refers to physically discrete units suitable as unitary dosage for warm-blooded animal subjects, each unit containing a predetermined quantity of active component calculated to produce the desired therapeutic effect in association with the required pharmaceutical diluent, carrier or vehicle. The specification for the novel dosage forms of this invention are indicated by characteristics of the active component and the particular therapeutic effect to be achieved or the limitations inherent in the art of compounding such an active component for therapeutic use in warm-blooded animals as disclosed in this specification. Examples of suitable oral dosage forms in accord with this invention are tablets, capsules, pills, powder packets, granules, wafers, cachets, teaspoonfuls, dropperfuls, ampules, vials, segregated multiples of any of the foregoing and other forms as herein described.

The complement modulating activity of compounds of this invention has been demonstrated by one or more of the following identified tests: (i) Test Code 026 (C1 inhibitor)—This test measures the ability of activated human C1 to destroy fluid phase human C2 in the presence of C4 and appropriate dilutions of the test compound. An active inhibitor protects C2 from C1 and C4; (ii) Test Code 035 (C3–C9 inhibitor)—This test determines the ability of the late components of human complement (C3–C9) to lyse EAC 142 in the presence of appropriate dilutions of the test compound. An active inhibitor protects EAC 142 from lysis by human C3–C9; (iii) Cap 50 Test—Here, appropriate amounts of the test compound are added to a pool of guinea pig or human serum in vitro, after which the undiluted serum capillary tube assay of U.S. Pat. No. 3,876,376 is run. The concentration of compound inhibiting 50% is reported; and (iv) Guinea Pig Intraperitoneal Test (GPIP)—Guinea pigs weighing about 300 g are dosed intraperitoneally (i.p.) with 200 mg/kg of the test compound dissolved in saline and adjusted to pH 7–8. Approximately 0.4 ml blood samples, taken by orbital sinus puncture 2 hours and 6 hours after injections, are collected directly into centrifuge tubes; 5 ml blood samples, taken by decapitation 24 hours after injection, are collected directly into beakers. The samples are allowed to clot, centrifuged, and the resultant sera are assayed for complement activity using the capillary complement assay. Percent inhibition is calculated by comparison with simultaneous controls. The results of the GPIP appear in Table I together with results of Test Code 026, 035, and Cap 50. Table I shows that the principal compounds of the invention possess highly significant complement modulating activity in warm-blooded animals.

-continued

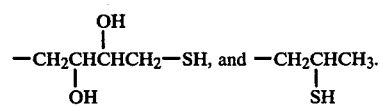

2. The compound according to claim 1, 2,3-dihydroxy-4-mercaptobutyl 2,3,6-tri-O-sulfo-4-O-(2,3,4,6-tetra-O-sulfo-α-D-glucopyranosyl)-1-thio-β-D-glucopyranoside heptasodium salt, having the structure:

TABLE I

| | Biological Activities | | | | | | |
|---|---|---|---|---|---|---|---|
| | In vitro Activity | | | | In vivo Activity Guinea Pig % Inhibition Intraperitoneal Time (Hours) | | |
| | Cl 026* | C-Late 035* | Guinea Pig | Human | | | |
| Compound | Wells | Wells | Cap 50 | Cap 50 | 2 | 6 | 24 |
| 2,3-Dihydroxy-4-mercaptobutyl 2,3,6-tri-O—sulfo-4-O—(2,3,4,6-tetra-O—sulfo-α-D-glucopyranosyl)-1-thio-β-D-glucopyranoside heptasodium salt | 12** | | | | | | |
| 3-Hydroxy-2-mercaptopropyl 2,3,6-tri-O—sulfo-4-O—(2,3,4,6-tetra-O—sulfo-α-D-glucopyranosyl-1-thio-β-D-glucopyranoside nonasodium salt | 9 | 3 | 142 79 200 | 6 | 69 | 70 | 3 |
| S—[2,3,6-tri-O—sulfo-4-O—(2,3,4,6-tetra-O—sulfo-α-D-glucopyranosyl)-β-D-glucopyranosyl]-L-cysteine heptasodium salt | 1 | | | | | | |
| S—[2,3,6-tri-O—sulfo-4-O—(2,3,4,6-tetra-O—sulfo-α-D-glucopyranosyl)-β-D-glucopyranosyl]-2-acetamido-4-mercaptobutyric acid heptasodium salt | 6 | | | | | | |
| 3-Hydroxy-2-mercaptopropyl 4-O—α-D-2',6'-O—sulfo-glucopyranosyl-1-thio-β-D-2,6-O—sulfo-glucopyranoside | 6 9 | | 268 500 | | | | |

*Tests identified by code herein. For a discussion of the tests, see "Systematic Discovery & Evaluation of Complement Inhibitors," N. Bauman et al., Immunopharmacology 3: 317-24 (1981).
**Activity in wells, a serial dilution assay; higher well number indicates higher activity. The serial dilutions are two-fold.

We claim:
1. A compound selected from those of the formula:

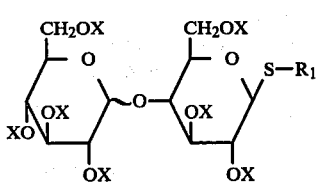

( —— = α or β)

wherein X is —SO₃M and M is a nontoxic pharmaceutically acceptable cation salt, wherein the salt forming moiety is selected from the group consisting of alkali metal, alkaline earth metal, aluminum, ammonia, zinc and substituted ammonia selected from the group consisting of trialkylamine (C₁-C₆), piperidine, pyrazine, alkanolamine (C₂-C₆) and cycloalkylamine (C₃-C₆); and R₁ is selected from the group consisting of

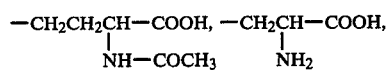

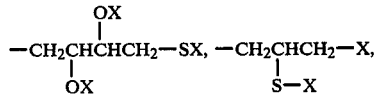

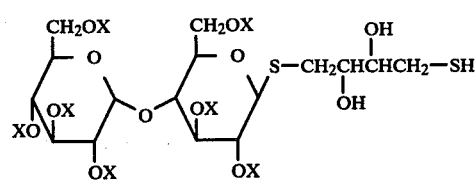

where X is —SO₃Na.

3. The compound according to claim 1, 2,3-dihydroxy-4-mercaptobutyl 2,3,6-tri-O-sulfo-4-O-(2,3,4,6-tetra-O-sulfo-α-D-glucopyranosyl)-1-thio-β-D-glucopyranoside heptatriethylammonium salt, having the structure:

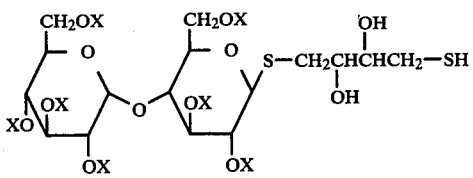

where X is —SO₃⁻NH⁺(C₂H₅)₃.

4. The compound according to claim 1, 3-hydroxy-2-mercaptopropyl 2,3,6-tri-O-sulfo-4-O-(2,3,4,6-tetra-O- sulfo-α-D-glucopyranosyl)-1-thio-β-D-glucopyrano-
side nonasodium salt, having the structure:

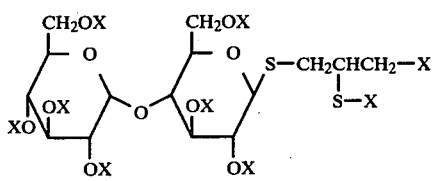

where X is —SO₃Na.

5. The compound according to claim 1, 3-hydroxy-2-mercaptopropyl 2,3,6-tri-O-sulfo-4-O-(2,3,4,6-tetra-O-sulfo-α-D-glucopyranosyl)-1-thio-β-D-glucopyrano-side nonatriethylammonium salt, having the structure:

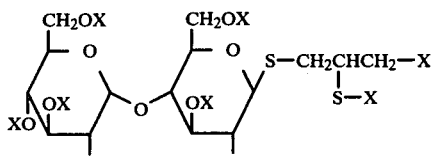

where X is —SO₃⁻NH⁺(C₂H₅)₃.

6. The compound according to claim 1, S-[2,3,6-tri-O-sulfo-4-O-(2,3,4,6-tetra-O-sulfo-α-D-glucopyranosyl)-β-D-glucopyranosyl]-L-cysteine heptasodium salt, having the structure:

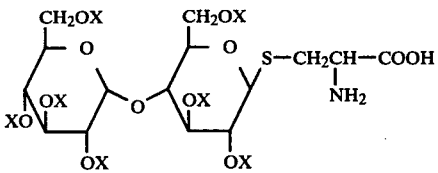

where X is —SO₃Na.

7. The compound according to claim 1, S-[2,3,6-tri-O-sulfo-4-O-(2,3,4,6-tetra-O-sulfo-α-D-glucopyranosyl)-β-D-glucopyranosyl]-L-cysteine heptatriethylam-monium salt, having the structure:

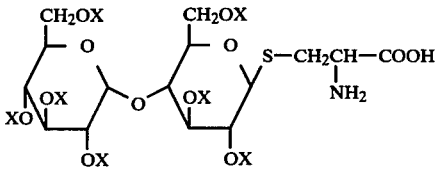

where X is —SO₃⁻NH⁺(C₂H₅)₃.

8. The compound according to claim 1, S-[2,3,6-tri-O-sulfo-4-O-(2,3,4,6-tetra-O-sulfo-α-D-glucopyranosyl)-β-D-glucopyranosyl]-2-acetamido-4-mercaptobutyric acid heptasodium salt, having the structure:

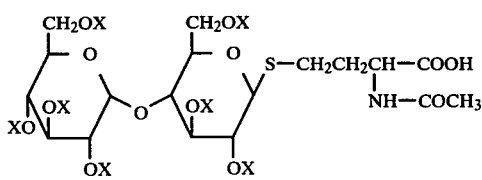

where X is —SO₃Na.

9. The compound according to claim 1, S-[2,3,6-tri-O-sulfo-4-O-(2,3,4,6-tetra-O-sulfo-α-D-glucopyranosyl)-β-D-glucopyranosyl]-2-acetamido-4-mercaptobutyric acid heptatriethylammonium salt, having the structure:

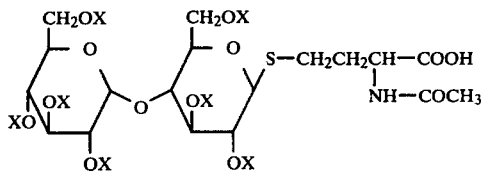

where X is —SO₃⁻NH⁺(C₂H₅)₃.

10. A compound selected from those of the formula:

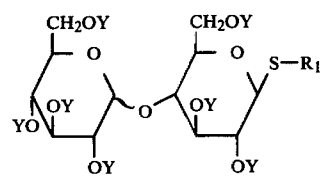

(∼ = α or β)

wherein Y is selected from the group consisting of hydrogen and —COCH₃ and R₁ is selected from the group consisting
of —CH₂CH₂CH—COOC(CH₃)₃,   —CH₂CH—COOC(CH₃)₃,
          |                           |
          NH—COCH₃                    NHCOOC(CH₃)₃

OH
              |
—CH₂CHCHCH₂—SH, and  —CH₂CHCH₂OH.
    |                      |
    OH                     SH 11. The compound according to claim 10, 2,3-dihydroxy-4-mercaptobutyl 2,3,6-tri-O-acetyl-4-O-(2,3,4,6-tetra-O-acetyl-α-D-glucopyranosyl)-1-thio-β-D-glucopyranoside, having the structure:

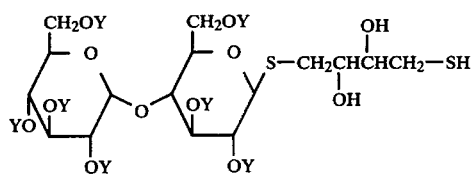

where Y is —COCH₃.

12. The compound according to claim 10, 2,3-dihydroxy-4-mercaptobutyl 4-O-(α-D-glucopyranosyl)-1-thio-β-D-glucopyranoside, having the structure:

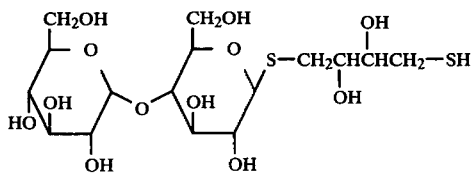

13. The compound according to claim 10, 3-hydroxy-2-mercaptopropyl 2,3,6-tri-O-acetyl-4-O-(2,3,4,6-tetra-O-acetyl-α-D-glucopyranosyl)-1-thio-β-D-glucopyranoside having the structure:

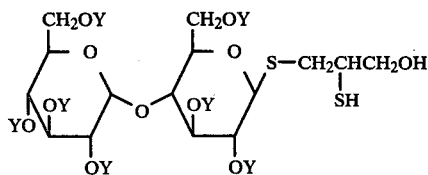

where Y is —COCH$_3$.

14. The compound according to claim 10, 3-hydroxy-2-mercaptobutyl 4-O-(α-D-glucopyranosyl)-1-thio-β-D-glucopyranoside having the structure:

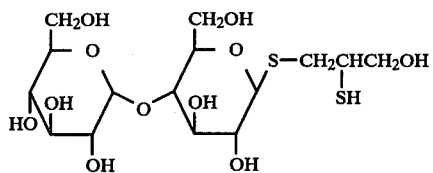

15. The compound according to claim 10, S-[2,3,6-tri-O-acetyl-4-O-(2,3,4,6-tetra-O-acetyl-α-D-glucopyranosyl)-β-D-glucopyranosyl]-L-N-tertiary-butyloxycabonyl tert. butyl ester, having the structure:

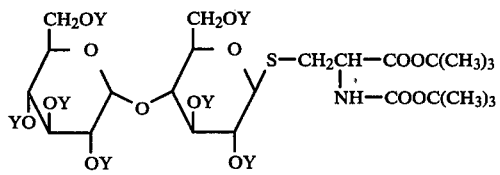

where Y is —COCH$_3$.

16. The compound according to claim 10, 4-O-(α-D-glucopyranosyl)-β-D-glucopyranosyl-L-N-tertiarybutyloxycarbonylcysteine, tertiary-butyl ester, having the structure:

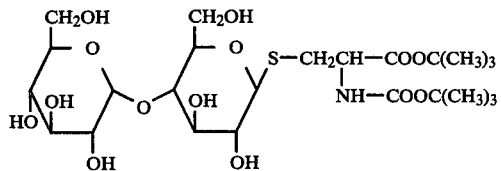

17. The compound according to claim 10, S-[2,3,6-tri-O-acetyl-4-O-(2,3,4,6-tetra-O-acetyl-α-D-glucopyranosyl)-β-D-glucopyranosyl]-2-acetamido-4-mercaptobutyric acid, tertiary-butyl ester, having the structure:

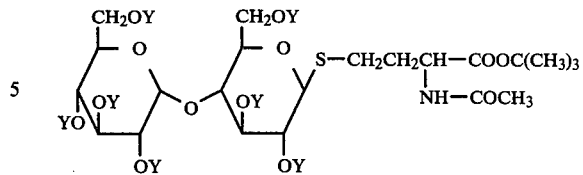

where Y is —COCH$_3$.

18. The compound according to claim 10, S-[4-O-(α-D-glucopyranosyl)-β-D-glucopyranosyl]-2-acetamido-4-mercaptobutyric acid, tertiary-butyl ester, having the structure:

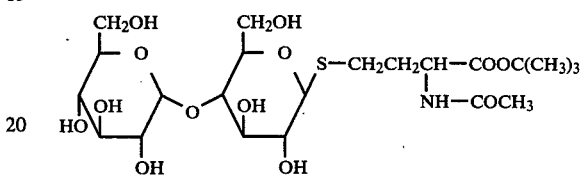

19. A method of modulating the complement system in a warm-blooded animal which comprises administering to said animal an effective complement modulating amount of a pharmaceutically acceptable compound selected from those of the formula:

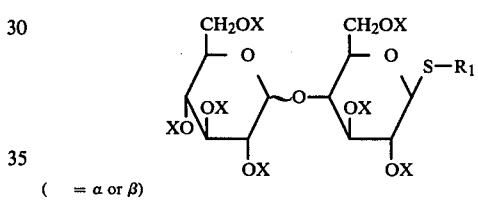

( = α or β)

wherein X is —SO$_3$M and M is a nontoxic pharmaceutically acceptable cation salt, wherein the salt forming moiety is selected from the group consisting of alkali metal, alkaline earth metal, aluminum, ammonia, zinc and substituted ammonia selected from the group consisting of trialkylamine (C$_1$-C$_6$), piperidine, pyrazine, alkanolamine (C$_2$-C$_6$) and cycloalkylamine (C$_3$-C$_6$); and R$_1$ is selected from the group consisting of

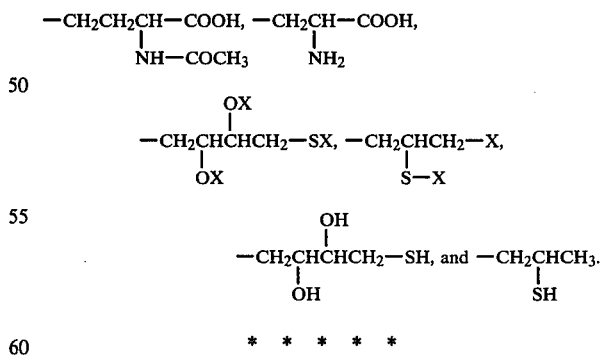

* * * * *

UNITED STATES PATENT AND TRADEMARK OFFICE
CERTIFICATE OF CORRECTION

PATENT NO. : 4,468,385
DATED : August 28, 1984
INVENTOR(S) : Francis Marc Callahan; Thomas Gary Miner; Seymour Bernstein It is certified that error appears in the above-identified patent and that said Letters Patent are hereby corrected as shown below:

Column 17, Claim 1, lines 45 to 50, that portion of the formula reading

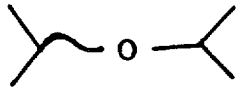   should read     ;

line 50, the portion "( = α or β )" should read -- ( ~ = α or β ) -- . Column 19, Claim 4, line 12, the portion italicized "--SO$_3$Na" should read -- --SO$_3$Na -- . Column 21, Claim 15, line 31, that portion of the chemical name reading "butyloxycabonyl" should read -- butyloxycarbonyl -- . Column 22, Claim 19, lines 30 to 35, that portion of the formula reading

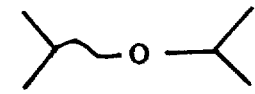   should read     ;

line 36, the portion "(= α or β )" should read -- (~ = α or β ) -- .

Signed and Sealed this

Twelfth Day of February 1985

[SEAL]

Attest:

DONALD J. QUIGG

Attesting Officer    Acting Commissioner of Patents and Trademarks